United States Patent
Webb et al.

(10) Patent No.: US 6,395,728 B2
(45) Date of Patent: *May 28, 2002

(54) METHOD OF TREATMENT AND PHARMACEUTICAL COMPOSITION

(75) Inventors: Randy Lee Webb, Flemington, NJ (US); Marc de Gasparo, Es Planches (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/757,413

(22) Filed: Jan. 9, 2001

Related U.S. Application Data

(62) Division of application No. 09/349,654, filed on Jul. 8, 1999, now Pat. No. 6,204,281.

(51) Int. Cl.⁷ .................. A61K 31/55; A61K 31/41
(52) U.S. Cl. .................. 514/212.04; 514/381
(58) Field of Search .................. 514/212.04, 381, 514/654

(56) References Cited

U.S. PATENT DOCUMENTS

| | | |
|---|---|---|
| 5,399,578 A | 3/1995 | Bühlmayer et al. |
| 5,492,904 A | 2/1996 | Wong |
| 5,721,263 A | 2/1998 | Inada et al. |
| 5,889,020 A | 3/1999 | Huxley et al. |
| 6,204,281 B1 * | 3/2001 | Webb et al. .......... 514/381 |

FOREIGN PATENT DOCUMENTS

| | | |
|---|---|---|
| WO | WO 92/10097 | 6/1992 |
| WO | WO 92/20342 | 11/1992 |

OTHER PUBLICATIONS

Dunlay Mc. et al., Journal of Human Hypertension, vol. 9, pp. 861–867 (1995).

Guidelines Subcommittee, Journal of Hypertension, vol. 17, pp. 151–183 (1999).

Prescribing information for Lotrel® (Dec. 1998).

Prescribing information for Diovan® (Jun., 1998).

Ruschitzka F.T. et al., American Heart Journal, vol. 134 (2), part II, pp. 531–547 (1997).

Corea et al.Clinical Pharmacology & Therapeutics, vol. 60, No. 3, pp. 341–346, (1996).

Chemical Abstracts No. 124:220073, Fujimura et al., (1996).

* cited by examiner

*Primary Examiner*—Raymond Henley, III
(74) *Attorney, Agent, or Firm*—Gregory D. Ferraro

(57) ABSTRACT

The invention relates to a method for the treatment or prevention of a condition or disease selected from the group consisting of hypertension, (acute and chronic) congestive heart failure, left ventricular dysfunction and hypertrophic cardiomyopathy, myocardial infarction and its sequelae, supraventricular and ventricular arrhythmias, atrial fibrillation or atrial flutter, atherosclerosis, angina (whether stable or ustable), renal insufficiency (diabetic and non-diabetic), heart failure, angina pectoris, diabetessecondary aldosteronism, primary and secondary pulmonary hyperaldosteronism, primary and pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, Raynaud's disease, luminal hyperplasia, cognitive dysfunction (such as Alzheimer's), and stroke, comprising administering a therapeutically effective amount of combination of (i) the $AT_1$-antagonists valsartan or a pharmaceutically acceptable salt thereof and (ii) a Calcium channel blocker or a pharmaceutically acceptable salt thereof and a pharmaceutically acceptable carrier to a mammal in need of such treatment and to corresponding pharmaceutical combination composition.

4 Claims, No Drawings

METHOD OF TREATMENT AND PHARMACEUTICAL COMPOSITION

This is a divisional application of U.S. application Ser. No. 09/349,654 filed Jul. 8, 1999, now U.S. Pat. No. 6,204,281.

The present invention relates to a pharmaceutical composition comprising as active ingredients (i) the $AT_1$ receptor antagonist (S)-N-(1-carboxy-2-methyl-prop-1-yl)-N-pentanoyl-N-[2'(1H-tetrazol-5-yl)biphenyl-4-yl-methyl]amine (valsartan) of formula (I)

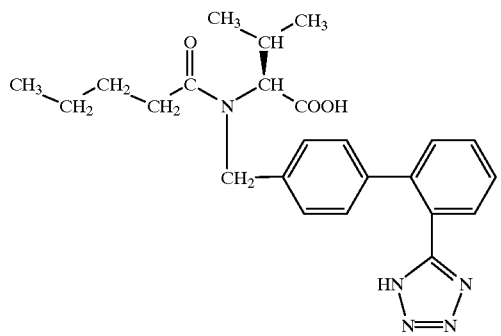

or a pharmaceutically acceptable salt thereof and (ii) a Calcium channel blocker (CCB) or a pharmaceutically acceptable salt thereof and (iii) a pharmaceutically acceptable carrier.

Valsartan is disclosed in EP 0443983 A.

A CCB useful in said combination is preferably selected from the group consisting of amlodipine, diltiazem, felodipine, fendiline, flunarizine, gallopamil, isradipine, lacidipine, mibefradil, nicardipine, nifedipine, niguldipine, niludipine, nimodipine, nisoldipine, nitrendipine, nivaldipine, ryosidine, tiapamil and verapamil, and in each case, a pharmaceutically acceptable salt thereof. All these drugs are therapeutically used as CCBs, e.g. as antihypertensive, anti-angina pectoris or anti-arrhythmic drugs.

Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred is amlodipine or a pharmaceutically acceptable salt, especially the besylate, thereof.

The compounds to be combined can be present as pharmaceutically acceptable salts. If these compounds have, for example, at least one basic centre, they can form acid addition salts. Corresponding acid addition salts can also be formed having, if desired, an additionally present basic centre. The compounds having at least one acid group (for example COOH) can also form salts with bases. Corresponding internal salts may furthermore be formed, if a compound of formula comprises e.g. both a carboxy and an amino group.

Preferred salts of corresponding CCBs are amlodipine besylate, diltiazem hydrochloride, fendiline hydrochloride, flunarizine di-hydrochloride, gallopamil hydrochloride, mibefradil di-hydrochloride, nicardipine hydrochloride, and verapamil hydrochloride.

The vasoconstrictive effects of angiotensin II are produced by its action on the non-striated smooth muscle cells, the stimulation of the formation of the adrenergic hormones epinephrine and norepinephrine as well as the increase of the activity of the sympathetic nervous system as a result of the formation of norepinephrine. Angiotensin II also has an influence on the electrolytic balance, produces e.g. antinatriuretic and antidiuretic effects in the kidney and thereby promotes the release of, on the one hand, the vasopressin peptide from the pituitary gland and, on the other hand, of aldosterone from the adrenal glomerulosa. All these influences play an important part in the regulation of blood pressure, in increasing both circulating volume and peripheral resistance. Angiotensin II is also involved in cell growth and migration and in extracellular matrix formation.

Angiotensin II interacts with specific receptors on the surface of the target cell. It has been possible to identify receptor subtypes which are termed e.g. $AT_1$- and $AT_2$-receptors. In recent times great efforts have been made to identify substances that bind to the $AT_1$-receptor. Such active ingredients are often termed angiotensin II antagonists. Because of the inhibition of the $AT_1$-receptor such antagonists can be used e.g. as antihypertensives or for the treatment of congestive heart failure.

Angiotensin II antagonists are therefore understood to be those active ingredients which bind to the $AT_1$-receptor subtype.

Prolonged and uncontrolled hypertensive vascular disease ultimately leads to a variety of pathological changes in target organs such as the heart and kidney. Sustained hypertension can lead as well to an increased occurrence of stroke. Therefore, there is a strong need to evaluate the efficacy of antihypertensive therapy, an examination of additional cardiovascular endpoints, beyond those of blood pressure lowering, to get further insight into the benefits of combined treatment.

The nature of hypertensive vascular diseases is multifactorial. Under certain circumstances, drugs with different mechanisms of action have been combined. However, just considering any combination of drugs having different mode of action does not necessarily lead to combinations with advantageous effects.

$AT_1$ antagonist and CCB reduce intracellular calcium by different and complementary mechanisms and facilitate the vasodilator effects of nitric oxide, being particularly effective in reversing endothelium dysfunction.

All the more surprising is the experimental finding that the combined administration of the $AT_1$-antagonist valsartan or a pharmaceutically acceptable salt thereof and a CCB or a pharmaceutically acceptable salt thereof results not only in a synergistic therapeutic effect but also in additional benefits resulting from combined treatment such as a surprising prolongation of efficacy and a broader variety of therapeutic treatment. This includes hemodynamic, antiproliferative, antithrombotic and antiatherogenic properties.

The measurement of cardiac mass to assess treatment-induced regression of hypertrophy provided data to support a supra-additive effect of combination of the present invention. Left ventricular hypertrophy is an independent risk factor for the development of myocardial infarction. Thus, effective blood pressure lowering coupled with the ability to regress or prevent the development of left ventricular hypertrophy has an impact on two important and contributing factors for heart failure.

Further benefits are that lower doses of the individual drugs to be combined according to the present invention can be used to reduce the dosage, for example, that the dosages need not only often be smaller but are also applied less frequently, or can be used to diminish the incidence of side effects. This is in accordance with the desires and requirements of the patients to be treated.

It can be shown that combination therapy with valsartan and a calcium channel blocker results in a more effective antihypertensive therapy (whether for malignant, essential, reno-vascular, diabetic, isolated systolic, or other secondary type of hypertension) through improved efficacy as well as a greater responder rate. The combination is also be useful in the treatment or prevention of (acute and chronic) congestive heart failure, left ventricular dysfunction and hypertrophic cardiomyopathy, diabetic cardiac myopathy, supraventricular and ventricular arrhythmias, atrial fibrillation or atrial flutter. It can further be shown that a valsartan+CCB therapy proves to be beneficial in the treatment and prevention of myocardial infarction and its sequelae. A valsartan plus CCB combination is also useful in treating atherosclerosis, angina (whether stable or unstable), and renal insufficiency (diabetic and non-diabetic). Furthermore, combination therapy using valsartan and a CCB can improve endothelial dysfunction, thereby providing benefit in diseases in which normal endothelial function is disrupted such as heart failure, angina pectoris and diabetes. Furthermore, the combination of the present invention may be used for the treatment or prevention of secondary aldosteronism, primary and secondary pulmonary hyperaldosteronism, primary and pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, Raynaud's disease, luminal hyperplasia, cognitive dysfunction (such as Alzheimer's), and stroke.

The person skilled in the pertinent art is fully enabled to select a relevant test model to prove the hereinbefore and hereinafter indicated therapeutic indications.

Representative studies are carried out with a combination of valsartan and amlodipine, e.g. applying following methodology. All experiments are performed in spontaneously hypertensive rats (SHR) supplied by Taconic Farms, Germantown, N.Y. (Tac:N(SHR)fBR). A radiotelemetric device (Data Sciences International, Inc., St. Paul, Minn.) is implanted into the lower abdominal aorta of all test animals between the ages of 14 to 16 weeks of age. All SHR are allowed to recover from the surgical implantation procedure for at least 2 weeks prior to the initiation of the experiments. The radiotransmitter is fastened ventrally to the musculature of the inner abdominal wall with a silk suture to prevent movement. Cardiovascular parameters are continuously monitored via the radiotransmitter and transmitted to a receiver where the digitized signal is then collected and stored using a computerized data acquisition system. Blood pressure (mean arterial, systolic and diastolic pressure) and heart rate are monitored in conscious, freely moving and undisturbed SHR in their home cages. The arterial blood pressure and heart rate are measured every 10 minutes for 10 seconds and recorded. Data reported for each rat represent the mean values averaged over a 24 hour period and are made up of the 144-10 minute samples collected each day. The baseline values for blood pressure and heart rate consist of the average of three consecutive 24 hour readings taken prior to initiating the drug treatments. All rats are individually housed in a temperature and humidity controlled room and are maintained on a 12 hour light/dark cycle.

In addition to the cardiovascular parameters, weekly determinations of body weight also are recorded in all rats. Since all treatments are administered in the drinking water, water consumption is measured five times per week. Valsartan and amlodipine doses for individual rats are then calculated based on water consumption for each rat, the concentration of drug substance in the drinking water, and individual body weights. All drug solutions in the drinking water are made up fresh every three to four days.

Upon completion of the 6 week treatment, SHR are anesthetized and the heart rapidly removed. After separation and removal of the atrial appendages, left ventricle and left plus right ventricle (total) are weighed and recorded. Left ventricular and total ventricular mass are then normalized to body weight and reported. All values reported for blood pressure and cardiac mass represent the group mean+sem.

Valsartan and amlodipine are administered via the drinking water either alone or in combination to SHR beginning at 18 weeks of age and continued for 6 weeks. Based on a factorial design, seven (7) treatment groups are used to evaluate the effects of combination therapy on blood pressure and heart rate. Treatment groups consist of valsartan alone in drinking water at a concentration of 240 mg/liter (high dose), amlodipine alone at a concentration of 120 mg/liter (high dose), valsartan (120 mg/liter)+amlodipine (60), valsartan (120)+amlodipine (120), valsartan (240)+amlodipine (60), valsartan (240)+amlodipine (120) and a vehicle control group on regular drinking water. Thus, 4 groups of SHR receive combination therapy.

Studies have been performed in SHR and demonstrate that the addition of a CCB confers additional benefit over that of valsartan monotherapy. The Area Under the Curve (AUC) for blood pressure reflects the changes in response to 6 week treatment in conscious SHR. Upon completion of the 6 week treatment period, hearts are removed for assessment of left ventricle mass and normalized to body weight.

The available results indicate an unexpected beneficial effect of a combination according to the invention.

Further representative studies are carried out with a combination of valsartan and a CCB, especially a non-DHP representative thereof, such as verapamil.

Diabetic renal disease is the leading cause of end-stage renal diseases. Hypertension is a major determinant of the rate of progression of diabetic diseases, especially diabetic nephropathy. It is known that a reduction of blood pressure may slow the reduction of diabetic nephropathy and proteinuria in diabetic patients, however dependent on the kind of antihypertensive administered.

In diabetic SHRs the presence of hypertension is an important determinant of renal injury, manifesting in functional changes such as albuminuria and in ultrastructural injury. For example, diabetic SHRs show ventricular hypertrophy and develop nephropathy resulting in sudden death events. Acordingly, the use of this animal model is well-applied in the art and suitable for evaluating effects of drugs on the development of diabetic renal diseases. There is a strong need to achieve a significant increase of the survival rate by treatment of hypertension in diabetes especially in NIDDM. It is known that CCBs are not considered as first line antihypertensives e.g. in NIDDM treatment. Though some kind of reduction of blood pressure may be achieved with CCBs, they may not be indicated for the treatment of renal disorders associated with diabetes. Surprisingly, treatment of diabetes associated with hypertension with the combination of valsartan and a CCB, especially a non-DHP, preferably verapamil, proved to result in the considerable reduction of sudden death events and consequently in a significant degree of increase of the survival rate in the experimental model using diabetic SHRs.

Diabetes is induced in SHRs aged about 6 to 8 weeks weighing about 250 to 300 g by treatment e.g. with streptozotocin. The drugs are administered by twice daily average. Untreated diabetic SHRs are used as control group (group 1). Other groups of diabetic SHRs are treated with 30 mg/kg of valsartan (group 2), with 20 mg/kg of verapamil (group 3) and with a combination of 20 mg/kg of valsartan and 15 mg/kg of verapamil (group 4). On a regular basis, besides other parameters the survival rate after 21 weeks of treatment is being monitored. In week 21 of the study, following survival rates have been determined:

| Test Group | Survival Rate [%] |
|---|---|
| 1 | 29.7 |
| 2 | 45.9 |
| 3 | 42.9 |
| 4 | 67.1 |

The results of this study clearly show, that though CCBs are not normally used for the treatment of hypertension in diabetic patients, not only the blood pressure is reduced but moreover the survival rate is drastically increased when administering to diabetic SHRs a combination of valsartan and verapamil (the amounts of both components in the combination being reduced versus the amounts of the single drugs when administered alone). The increased survival seen in diabetic SHR is consistent with an attenuation of end-organ damage. Accordingly, the combination of valsartan and a CCB may be used for the treatment (and also for the prevention) of diabetes, e.g. of hypertension in diabetic patients, especially in hypertensive patients with NIDDM, and may be used for slowing the progression of diabetic renal diseases, such as diabetic nephropathy associated with NIDDM, and for reducing proteinuria in diabetic patients.

It is the object of this invention to provide a pharmaceutical combination composition, e.g. for the treatment or prevention of a condition or disease selected from the group consisting of hypertension, (acute and chronic) congestive heart failure, left ventricular dysfunction and hypertrophic cardiomyopathy, diabetic cardiac myopathy, supraventricular and ventricular arrhythmias, atrial fibrillation or atrial flutter, myocardial infarction and its sequelae, atherosclerosis, angina (whether unstable or stable), renal insufficiency (diabetic and non-diabetic), heart failure, angina pectoris, diabetessecondary aldosteronism, primary and secondary pulmonary hyperaldosteronism, primary and pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, Raynaud's disease, luminal hyperplasia, cognitive dysfunction (such as Alzheimer's), and stroke which composition comprises (i) the $AT_1$-antagonists valsartan or a pharmaceutically acceptable salt thereof and (ii) a CCB or a pharmaceutically acceptable salt thereof and a pharmaceutically acceptable carrier.

In this composition, components (i) and (ii) can be obtained and administered together, one after the other or separately in one combined unit dose form or in two separate unit dose forms. The unit dose form may also be a fixed combination.

A further aspect of the present invention is the use a pharmaceutical composition comprising (i) the $AT_1$-antagonists valsartan or a pharmaceutically acceptable salt thereof and (ii) a CCB or a pharmaceutically acceptable salt thereof and a pharmaceutically acceptable carrier for the manufacture of a therapeutically effective pharmaceutical composition for the treatment or prevention of a condition or disease selected from the group consisting of hypertension, (acute and chronic) congestive heart failure, left ventricular dysfunction and hypertrophic cardiomyopathy, myocardial infarction and its sequelae, supraventricular and ventricular arrhythmias, atrial fibrillation or atrial flutter, atherosclerosis, stable angina (whether stabel or unstable), renal insufficiency (diabetic and non-diabetic), heart failure, angina pectoris, diabetessecondary aldosteronism, primary and secondary pulmonary hyperaldosteronism, primary and pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, Raynaud's disease, luminal hyperplasia, cognitive dysfunction (such as Alzheimer's), and stroke A further aspect of the present invention is a method for the treatment or prevention of a condition or disease selected from the group consisting of hypertension, (acute and chronic) congestive heart failure, left ventricular dysfunction and hypertrophic cardiomyopathy, myocardial infarction and its sequelae, supraventricular and ventricular arrhythmias, atrial fibrillation or atrial flutter, atherosclerosis, angina (whether stable or ustable), renal insufficiency (diabetic and non-diabetic), heart failure, angina pectoris, diabetessecondary aldosteronism, primary and secondary pulmonary hyperaldosteronism, primary and pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, Raynaud's disease, luminal hyperplasia, cognitive dysfunction (such as Alzheimer's), and stroke, comprising administering a therapeutically effective amount of combination of (i) the $AT_1$-antagonists valsartan or a pharmaceutically acceptable salt thereof and (ii) a CCB or a pharmaceutically acceptable salt thereof and a pharmaceutically acceptable carrier to a mammal in need of such treatment.

A therapeutically effective amount of each of the component of the combination of the present invention may be administered simultaneously or sequentially and in any order.

The corresponding active ingredient or a pharmaceutically acceptable salt thereof may also be used in form of a hydrate or include other solvents used for crystallization.

The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carries, especially suitable for enteral or parenteral application.

The novel pharmaceutical preparations contain, for example, from about 10% to about 80%, preferably from about 20% to about 60%, of the active ingredient. Pharmaceutical preparations according to the invention for enteral or parenteral administration are, for example, those in unit dose forms, such as sugar-coated tablets, tablets, capsules or suppositories, and furthermore ampoules. These are prepared in a manner known per se, for example by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

The determination of the dose of the active ingredients necessary to achieve the desired therapeutic effect is within the skill of those who practice in the art. The dose depends on the warm-blooded animal species, the age and the individual condition and on the manner of administration. In the normal case, an approximate daily dose in the case of oral administration for a patient weighing approximately 75 kg for oral application is of about 10 mg to about 200 mg, especially about 20 to about 120 mg, most preferably about 40 mg to about 80 mg for valsartan and about 1.0 mg to about 180 mg, preferably about 2.5 mg to about 50 mg, for the CCB, depending on the specific CCB.

The following example illustrates the invention described above; however, it is not intended to limit its extent in any manner.

Valsartan Tablet Formulation 80 mg+Amlodipine 5 mg (Rollercompaction)

| Dosage (mg) | 80 mg Valsartan + 5 mg Amlodipine |
|---|---|
| Diameter (mm) | 9 |
| Shape | round |
| Breaking line | without |
| Tablet-weight (mg) | 215 |

Formulation of the Tablet Valsartan 80 mg+Amlodipine 5 mg

| Dosage Strength | Function of the Excipient in the Formulation | 80 mg Valsartan + 5 mg Amlodipine mg: |
|---|---|---|
| I. Compactate | | |
| 1. Valsartan DS | drug substance | 80.0 |
| 2. Amlodipine DS | drug substance | 5.0 |
| 3. Avicel PH 102 | filler | 104.0 |
| 4. PVPP-XL | disintegrant | 20.0 |
| 5. Aerosil 200 | glidant | 0.75 |
| 6. Magnesium-stearate | lubricant | 2.5 |
| II. Outer Phase | | |
| 7. Aerosil 200 | glidant | 0.75 |
| 8. magnesium-stearate | lubricant | 2.0 |
| total | | 215.0 |

What is claimed is:

1. A method for the treatment or prevention of hypertension associated with diabetes comprising administering a therapeutically effective amount of a combination consisting essentially of (i) the $AT_1$-antagonist valsartan or a pharmaceutically acceptable salt thereof and (ii) the Calcium channel blocker amlodipine or a pharmaceutically acceptable salt thereof, and a pharmaceutically acceptable carrier to a mammal in need thereof.

2. A pharmaceutical combination composition consisting essentially of (i) the $AT_1$-antagonist valsartan or a pharmaceutically acceptable salt thereof and (ii) the Calcium channel blocker amlodipine or a pharmaceutically acceptable salt thereof and a pharmaceutically acceptable carrier.

3. A pharmaceutical combination composition as claimed in claim 2 for oral application, comprising of about 10 mg to about 200 mg of valsartan.

4. A pharmaceutical combination composition as claimed in claim 2 for oral application, comprising about 1.0 mg to about 180 mg of the Calcium channel blocker amlodipine.

* * * * *